(12) United States Patent
Reddy et al.

(10) Patent No.: US 8,664,272 B2
(45) Date of Patent: Mar. 4, 2014

(54) COMPOSITION AND METHODS FOR THE TREATMENT OF MYELODYSPLASTIC SYNDROME AND ACUTE MYELOID LEUKEMIA

(75) Inventors: E. Premkumar Reddy, Villanova, PA (US); M. V. Ramana Reddy, Upper Darby, PA (US); James F. Holland, Scarsdale, NY (US); Lewis R. Silverman, Sleepy Hollow, NY (US); Svetlana Zinzar, New York, NY (US)

(73) Assignees: Temple University—Of the Commonwealth System of Higher Education, Philadelphia, PA (US); Icahn School of Medicine at Mount Sinai, New York, NY (US)

( * ) Notice: Subject to any disclaimer, the term of this patent is extended or adjusted under 35 U.S.C. 154(b) by 661 days.

(21) Appl. No.: 12/310,575

(22) PCT Filed: Aug. 30, 2006

(86) PCT No.: PCT/US2006/034093
§ 371 (c)(1),
(2), (4) Date: Feb. 27, 2009

(87) PCT Pub. No.: WO2008/027049
PCT Pub. Date: Mar. 6, 2008

(65) Prior Publication Data
US 2010/0305059 A1 Dec. 2, 2010

(51) Int. Cl.
C07C 317/10 (2006.01)
C07C 229/34 (2006.01)
C07C 317/28 (2006.01)

(52) U.S. Cl.
CPC .................. *C07C 317/28* (2013.01)
USPC .......................... 514/562; 564/440

(58) Field of Classification Search
None
See application file for complete search history.

(56) References Cited

U.S. PATENT DOCUMENTS

| | | | |
|---|---|---|---|
| 6,359,013 B1 | 3/2002 | Reddy et al. | 514/710 |
| 6,486,210 B2 | 11/2002 | Reddy et al. | 514/708 |
| 6,541,475 B2 | 4/2003 | Reddy et al. | 514/252.12 |
| 6,548,553 B2 | 4/2003 | Reddy et al. | 514/710 |
| 6,576,675 B1 | 6/2003 | Reddy et al. | 514/710 |
| 6,599,932 B1 | 7/2003 | Reddy et al. | 514/438 |
| 6,646,009 B2 | 11/2003 | Reddy et al. | 514/604 |
| 6,656,973 B2 | 12/2003 | Cosenza et al. | 514/710 |
| 6,667,346 B2 | 12/2003 | Reddy et al. | 514/710 |
| 6,762,207 B1 | 7/2004 | Reddy et al. | 514/709 |
| 6,767,926 B1 | 7/2004 | Cosenza et al. | 514/710 |
| 6,787,667 B2 | 9/2004 | Reddy et al. | 562/429 |
| 7,053,123 B2 | 5/2006 | Reddy et al. | 514/710 |
| 7,056,953 B2 | 6/2006 | Reddy et al. | 514/710 |
| 2003/0114538 A1 | 6/2003 | Reddy et al. | 514/709 |
| 2003/0166270 A1 | 9/2003 | Reddy et al. | 435/325 |
| 2004/0203067 A1 | 10/2004 | Reddy et al. | 435/6 |
| 2004/0229959 A1 | 11/2004 | Reddy et al. | 514/710 |
| 2005/0130942 A1 | 6/2005 | Reddy et al. | 514/114 |
| 2005/0159347 A1 | 7/2005 | DiMartino | 514/9 |
| 2006/0167317 A1 | 7/2006 | Reddy et al. | 564/211 |
| 2008/0161252 A1 | 7/2008 | Reddy et al. | 514/34 |

FOREIGN PATENT DOCUMENTS

| | | | | |
|---|---|---|---|---|
| WO | WO2006/010152 | * | 1/2006 | A61K 31/195 |
| WO | WO 2006/091870 A2 | | 8/2006 | C07C 311/37 |
| WO | WO2006/104668 | * | 10/2006 | A61K 31/704 |

OTHER PUBLICATIONS

Sulewska et al., "DNA methylation in states of cell physiology and pathology" Folia Biochemica et Cytobiologica (2007) vol. 45 No. 3, pp. 149-158.*
Karon et al., "5-Azacytidine: A New Active Agent for the Treatment of Acute Leukemia" Blood (1973) vol. 42 No. 3 pp. 359-365.*
Silverman et al., "Randomized Controlled Trial of Azacitidine in Patients With the Myelodysplastic Syndrome: A Study of the Cancer and Leukemia Group B" Journal of Clinical Oncology (2002) vol. 20 No. 10 pp. 2429-2440.*
Wijermans et al., "Low-Dose 5-Aza-2*-Deoxycytidine, a DNA Hypomethylating Agent, for the Treatment of High-Risk Myelodysplastic Syndrome: A Multicenter Phase II Study in Elderly Patients" Journal of Clinical Oncology (2000) vol. 18 No. 5 pp. 956-962.*
Skidan I, Zinzar S, Holland JF, Reddy R, Reddy EP, Silverman LR. Toxicology of a novel small molecule ON1910Na on human bone marrow and leukemic cells in vitro [abstract]. In: Proceedings of the 97th Annual Meeting of the American Association for Cancer Research; Apr. 2, 2006; Washington, DC. Philadelphia (PA): AACR; Mar. 3, 2006. p. 6. Abstract nr 1310.
Gumireddy, et al. "ON01910, a non-ATP-competitive small molecule inhibitor of Plk1, is a potent anticancer agent", *Cancer Cell*, vol. 7:275-286 (Mar. 14, 2005).

(Continued)

Primary Examiner — Eric S Olson
(74) Attorney, Agent, or Firm — Drinker Biddle & Reath LLP

(57) ABSTRACT

Methods and compositions are provided for treating myelodysplastic syndrome and acute myeloid leukemia, wherein the composition comprises at least one compound according to Formula I:

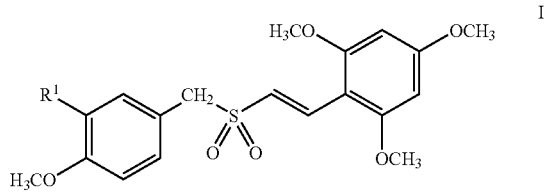

wherein $R^1$ is selected from the group consisting of $-NH_2$, $-NH-CH_2-CO_2H$, $-NH-CH(CH_3)-CO_2H$, and $-NH-C(CH_3)_2-CO_2H$, or a pharmaceutically acceptable salt of such a compound; and a DNA methyltransferase inhibitor, or a pharmaceutically acceptable salt thereof.

30 Claims, No Drawings

(56) References Cited

OTHER PUBLICATIONS

E. Alessandrino et al., "Myelodysplastic syndromes: recent advances", *haematologica* 2001; 86: 1124-1157.
Vidaza™; Pharmion Corporation, Boulder, CO (Aug. 2004).
L. Silverman, MD, "The myelodysplastic Syndrome", *Cancer Medicine* 2003; NCBI.
S. Castellino, MD, FAAP et al., "Myelodysplasia", *emedicine* 2003; 1-15.
Dr. G. Quade, "Myelodysplastic Syndromes", *National Cancer Institute* 2005; 1-14.
Dr. G. Quade, "Adult Acute Myeloid Leukemia", *National Cancer Institute* 2005; 1-36.
P. L. Greenburg et al., "Myelodysplastic Syndromes", *American Society of Hematology* 2002; 136-161.
M. Sullivan et al., "Azacitidine: A novel agent for myelodysplastic syndromes", *Am. J. Health-Syst. Pharm.* 2005; 62: 1567-1573.
K. Seiter, MD et al., "Acute Myelogenous Leukemia", *emedicine* 2006; 1-31.
C. A. Schiffer, MD et al., "Acute Myeloid Leukemia in Adults", *Cancer Medicine* 2003; NCBI.
C. B. Yoo et al., "Epigenetic therapy of cancer: past, present and future", *Nature Reviews/Drug Discovery* 2006; 5: 37-50.
L. R. Silverman, M.D., "The Role of Methyltransferase Inhibitors in the Management of the Myelodysplastic Syndromes", *Cancer Control* 2004; 11(6): 11-15.
A. List, M.D., "Methyltransferase Inhibitors: Changing the Treatment Algorithm for Myelodysplastic Syndromes", *Cancer Control* 2004; 11(6): 16-19.
B. Brueckner et al., "DNA methyltransferase inhibitors: old and new drugs for an epigenetic cancer therapy", *TRENDS in Pharmacological Sciences* 2004; 25(11): 551-554.
M. Goffin et al., "DNA methyltransferase inhibitors—state of the art", *Annals of Oncology* 2002; 13: 1699-1716.
G. Leone et al., "DNA methylation and demethylating drugs in myelodysplastic syndromes and secondary leukemias", *haematologica* 2002; 87: 1324-1341.
M. A. A. Siddiqui et al., "Azacitidine in Myelodysplastic Syndromes", *Drugs* 2005; 65(13): 1781-1789.
G. Mufti et al., "Myelodysplastic Syndrome", in *Hematology 2003, American Society of Hematology 2003*; 176-199.
R. Ohno, "How High Can We Increase Complete Remission Rate in Adult Acute Myeloid Leukemia?", International Journal of Hematology 2000; 72: 272-279.

\* cited by examiner

COMPOSITION AND METHODS FOR THE TREATMENT OF MYELODYSPLASTIC SYNDROME AND ACUTE MYELOID LEUKEMIA

FIELD OF THE INVENTION

The invention relates to a method for treating leukemia and pre-leukemic blood disorders by administering a combination of agents.

BACKGROUND OF THE INVENTION

Therapy for cancer has advanced significantly. Many proliferative disorders can now be effectively treated by administering therapeutic agents that include natural products, derivatives of natural products and synthetic compounds. Therapy for proliferative disorders, particularly cancer chemotherapy, may comprise administration of a combination of agents.

I. Myelodysplastic Syndromes and Myeloid Leukemias

Myelodysplastic syndrome (MDS), derived from a multipotent hematopoietic stem cell, is characterized clinically by a hyperproliferative bone marrow, reflective of ineffective hematopoiesis, and is accompanied by one or more peripheral blood cytopenias. Bone marrow failure results, leading to death from bleeding and infection in the majority, while transformation to acute leukemia occurs in up to 40% of patients. Because of the high rate of transformation to acute leukemia, myelodysplastic syndrome has also been termed "preleukaemia". Clinical aspects of the disease are reviewed by L. R. Silverman in *Cancer Medicine*, Ed. David W. Kufe et al., 6$^{th}$ Edition, B. C. Decker, 2003, the entire disclosure of which is incorporated herein by reference. See also: P. L. Greenberg, N. S. Young, and N. Gattermann, "Myelodysplastic Syndromes", *Hematology*, 2002, 136-61.

Estimates of the incidence of myelodysplastic syndrome range from 1 case per 100,000 per year to a frequency approximately equal to or greater than that of acute myeloid leukemia (AML) or approximately 14,000 new cases per year in the United States. The incidence appears to be increasing, which is probably due to a number of factors including greater awareness, greater diagnostic precision and the aging of the population.

The French-American-British (FAB) Study Group has recognized five categories of myelodysplastic syndrome based on morphologic characteristics and the percentage of blasts in the bone marrow and peripheral blood:

Refractory anemia (RA): Patients suffer from an anemia that is resistant or refractory to treatment with iron and/or vitamins, and there are less than 5% blasts in the marrow. There may be mild to moderate lowering of WBC and platelets as well.

Refractory anemia with ringed sideroblasts (RARS): Patients have a refractory anemia, and in addition, abnormal precursors of red cells containing iron deposits in the form of a ring around the nucleus called ringed sideroblasts make up more than 15% of the marrow cells. Blasts constitute less than 5% of the marrow.

Refractory anemia with excess blasts (RAEB): In this category, patients with refractory anemia also have either 1-5% circulating blasts in the peripheral blood or 5-20% blasts in their marrow.

Refractory anemia with excess blasts in transformation (RAEB-t): If the percentage of circulating blasts exceeds 5%, or there are 20-30% blasts in the bone marrow, the patients are considered as transforming towards acute leukemia.

Chronic myelomonocytic leukemia (CMML): While the bone marrow looks more or less similar to the other types of myelodysplastic syndrome, there is an increase in monocyte cells in both blood and marrow, and the total WBC count may also be increased. The blasts are between 5-20% in the bone marrow.

A classification system has also been developed by the World Health Organization, which can be related to the FAB classification as shown in Table 1.

TABLE 1

Classifications of Myelodysplastic Syndrome

| FAB Classification | WHO Classification |
|---|---|
| Refractory anemia (RA) | Refractory anemia (unilineage) 5q-syndrome Refractory cytopenia with multilineage dysplasia (RCMD) |
| Refractory anemia with ringed sideroblasts (RARS) | Refractory anemia with ringed sideroblasts (unilineage) 5q-syndrome Refractory cytopenia with multilineage dysplasia and ringed sideroblasts (RCMD-RS) |
| Refractory anemia with excess blasts (RAEB) | Refractory anemia with excess blasts I (RAEB-I) Refractory anemia with excess blasts II (RAEB-II) |
| Refractory anemia with excess blasts in transformation (RAEB-t) | (Classified as acute myeloid leukemia) |
| Chronic myelomonocytic leukemia (CMML) | Chronic myelomonocytic leukemia (CMML) Unclassifiable myelodysplastic syndrome |

The cellular elements of blood originate from the pluripotent hematopoietic stem cell. Stem cells have extensive regenerative and differentiating capacity and generate lymphoid and myeloid precursors, which then produce lymphocytes, neutrophils, eosinophils, basophils, erythrocytes, and platelets. In myelodysplastic syndrome, a dysregulation in the differentiation process appears to occur. Mortality in myelodysplastic syndrome is related to bleeding, recurrent infection, and leukemic transformation. In the absence of treatment, myelodysplastic syndrome can be a rapidly fatal disease, with or without the transformation to acute myeloid leukemia. An estimated 20-40% of adults with myelodysplastic syndrome develop leukemia, and 30-40% of myelodysplastic syndrome patients succumb to infection, bleeding, or both.

A prognostic scoring system, the International Prognostic Scoring System (IPSS), has been developed for patients with myelodysplastic syndrome. The IPSS is a consensus prognostic scoring system based on cytogenetic, morphological, and clinical data from seven large risk-based studies that had each generated prognostic systems. P. Greenberg, et al., "International Scoring System for Evaluating Prognosis in Myelodysplastic Syndromes", *Blood*, 1997, 89(6) 2079-88. Compared with prior risk-based classifications, the IPSS provides an improved method for evaluating prognosis in MDS. Based on univariate analysis it was found that the major variables having an impact on disease outcome for evolution to acute myeloid leukemia were cytogenetic abnormalities, the percentage of bone marrow myeloblasts, and the number of cytopenias. Factors for survival, in addition to the above variables, also included age and gender.

The cytogenetic subgroups of outcome were classified as follows:

"good" outcomes were normal, iY alone, del(5q) alone, del(20q) alone;

"poor" outcomes were complex (ie, δ3 abnormalities) or chromosome 7 anomalies;

"intermediate" outcomes were other abnormalities.

Multivariate analysis combined these cytogenetic subgroups with the percentage of bone marrow blasts and the number of cytopenias to generate a prognostic model. Weighting these variables by their statistical power separated patients into distinctive subgroups of risk for 25% evolution to acute myeloid leukemia:

low, 9.4 years;
intermediate-1 (INT-1), 3.3 years;
intermediate-2 (INT-2), 1.1 years; and
high, 0.2 year These same features also separated patients into similar distinctive risk groups for median survival:

low, 5.7 years;
INT-1, 3.5 years;
INT-2, 1.2 years; and
high, 0.4 year.

The IPSS scoring system for myelodysysplastic syndrome is summarized in Table 2. The correlation between the IPSS score and median survival and progression to acute myeloid leukemia is summarized in Table 3, which also shows that stratification of IPSS scores for age further improves analysis of survival.

TABLE 2

International Prognostic Scoring System (IPSS) for Myelodysplastic Syndrome Survival and Acute Myeloid Leukemia Progression.

| Prognostic Variable | Score Value | | | | |
|---|---|---|---|---|---|
| | 0 | 0.5 | 1.0 | 1.5 | 2.0 |
| Bone Marrow Blasts (%) | <5 | 5-10 | — | 11-20 | 21-30 |
| Karyotype* | Good | Intermediate | Poor | — | — |
| Cytopenias | 0/1 | 2/3 | — | — | — |

*Good: normal, -y, del(5q), del(20q); Poor: complex (≥3 abnormalities) or chromosome 7 abnormalities; Intermediate: all other abnormalities
Scores for risk groups are as follows: Low, 0; INT-1, 0.5-1.0; INT-2, 1.5-2.0; High ≥ 2.5.

TABLE 3

Age-Related Survival and Acute Myeloid Leukemia Evolution of Myelodysplastic Patients Within the IPSS Subgroups

| | No. of Patients | IPSS Classification | | | |
|---|---|---|---|---|---|
| | | Low | INT-1 | INT-2 | High |
| Median Survival (yr) | | | | | |
| Total no. of patients | 816 | 267 (33%) | 314 (38%) | 176 (22%) | 59 (7%) |
| Median (yr) Age | | 5.7 | 3.5 | 1.2 | 0.4 |
| ≤60 | 205 (25%) | 11.8 | 5.2 | 1.8 | 0.3 |
| >60 | 611 (75%) | 4.8 | 2.7 | 1.1 | 0.5 |
| ≤70 | 445 (54%) | 9.0 | 4.4 | 1.3 | 0.4 |
| >70 | 371 (46%) | 3.9 | 2.4 | 1.2 | 0.4 |
| 25% Acute Myeloid Leukemia Evolution (yr) | | | | | |
| Total no. of patients | 759 | 235 (31%) | 295 (39%) | 171 (22%) | 58 (8%) |
| Median (yr) Age | | 9.4 | 3.3 | 1.1 | 0.2 |
| ≤60 | 187 (25%) | >9.4 (NR) | 6.9 | 0.7 | 0.2 |
| >60 | 572 (75%) | 9.4 | 2.7 | 1.3 | 0.2 |
| ≤70 | 414 (55%) | >9.4 (NR) | 5.5 | 1.0 | 0.2 |
| >70 | 345 (45%) | >5.3 (NR) | 2.2 | 1.4 | 0.4 |

NR: Not reached (i.e. fewer than 25% of the patient group progressed to AML)

Acute myeloid leukemia is the most common variant of acute leukemia occurring in adults, comprising approximately 80-85% of cases of acute leukemia diagnosed in individuals greater than 20 years of age. The heterogeneous group of acute leukemic disorders of myeloid hematopoietic cells has been called a variety of names including acute myelogenous leukemia, acute myelocytic leukemia, acute myeloid leukemia, acute myeloblastic leukemia, acute granulocytic leukemia, and acute nonlymphocytic leukemia. The myeloid character of the malignant blasts can be determined by detection of characteristic morphologic and immunologic findings. A National Cancer Institute-sponsored workshop has suggested that the term acute myeloid leukemia (acute myeloid leukemia) is preferred. Clinical aspects of the disease are reviewed by C. A. Schiffer and R. M. Stone in *Cancer Medicine*, Ed. David W. Kufe et al., 6$^{th}$ Edition, B. C. Decker, 2003, the entire disclosure of which is incorporated herein by reference.

This French, American, and British (FAB) classification has been developed to diagnose and classify acute myeloid leukemia. The diagnosis of acute myeloid leukemia requires that myeloblasts constitute 30% (or 20% based on a recent World Health Organization (WHO) classification system) or more of bone marrow cells or circulating white blood cells. The hematologic properties of the disease, defines the various subtypes described below. The FAB nomenclature (M1 through M7) classifies the subtypes of acute myeloid leukemia according to the normal marrow elements that the blasts most closely resemble. Table 4 includes both the FAB classifications as well as additional classes recognized by the WHO.

TABLE 4

Classifications of Acute Myeloid Leukemia

Acute myeloid leukemia, minimally differentiated (MO)
Acute myeloid leukemia without maturation (M1)
Acute myeloid leukemia with maturation (M2)
Acute myeloid leukemia with maturation with t(8; 21)
Acute promyelocytic leukemia (M3)
Hypergranular type
Microgranular type
Acute myelomonocytic leukemia (M4)
Acute myelomonocytic leukemia with increased marrow eosinophils (M4EO)
Acute Monocytic Leukemia (M5)
Acute monoblastic leukemia (M5a)
Acute monocytic leukemia with maturation (M5b)
Erythroleukemia
Erythroid/myeloid) (M6a)
Pure erythroid malignancy (M6b)
Acute megakaryoblastic leukemia (M7)
Acute megakaryoblastic leukemia associated with t(1; 22)
Acute basophilic leukemia
Acute myelofibrosis (acute myelodysplasia with myelofibrosis)
Acute leukemia and transient myeloproliferative disorder in Down's Syndrome
Hypocellular acute myeloid leukemia
Myeloid sarcoma Although there have been gradual improvements in the complete remission (CR) rates worldwide in acute myeloid leukemia patients, this has not translated into improved outcomes, particularly for older patients. Reduced morbidity and mortality can be attributed to more widespread availability of sophisticated supportive care rather than new therapies. Relatively few changes in therapy have been made since the introduction of combined therapy with daunorubicin and cytosine arabinoside. Attempts to find new therapies have been disappointing. Combinations with alternative anthracyclines or other agents such as rubidizone, aclacinomycin, amsacrine, mitoxantrone, and idarubicin have been used in several trials, but none of these studies demonstrated a survival or disease-free survival advantage with these different agents. Overall, complete remission rates for treated patients are about 50-75%. However, in acute myeloid leukemia patients over 60 years of age the complete remission rate is only about 50%, with failures divided equally between drug resistant leukemia and deaths occurring during marrow aplasia as a consequence of reduced end organ tolerance. Complete remission can be achieved in only approximately 20%-30% of patients whose leukemia followed treatment for another cancer. Even if remission is achieved, however, because some leukemia cells usually remain, some form of therapy after complete remission is required to achieve long-term disease-free survival. Despite aggressive therapy, overall, only 20-30% of patients enjoy long-term disease-free survival.

In spite of advances that have occurred in the treatment of myelodysplastic syndrome and acute myeloid leukemia, it is clear that new approaches are needed to increase the fraction of patients cured.

II. Azacitidine and other DNA Methyltransferase Inhibitors

DNA Methyltransferase Inhibitors

DNA methylation is believed to play a key role in gene expression. DNA is methylated by DNA methyltransferases at the 5-position of the cytosine ring, almost exclusively in the context of CpG sites. CpG sites are regions of DNA where a cytosine nucleotide occurs next to a guanine nucleotide in the linear sequence of bases along its length. "CpG" stands for cytosine and guanine separated by a phosphate, which links the two nucleosides together in DNA. (The "CpG" notation is used to distinguish a cytosine followed by guanine from a cytosine base paired to a guanine.) The CpG sequence is relatively rare in eukaryotic genomes due to the action of DNA methyltransferases, which recognize these CpG sites and methylate the cytosine, turning it into 5-methylcytosine. Following spontaneous deamination, the 5-methylcytosine is converted into thymine.

However, there are regions of the DNA which have a high concentration of CpG sites. These regions, known as CpG islands, are found at the promoters of eukaryotic genes. These CpG sites are usually low in methylation. Methylation near the promoter sites inhibits gene expression.

DNA hypermethylation at CpG islands near the promoter region of genes is believed to be a key factor in diseases such as myelodysplastic syndrome, acute myeloid leukemia, and other malignancies because DNA methylation is a mechanism by which expression of genes can be inhibited. Thus, one approach to the treatment of such diseases has been the use of DNA methyltransferase inhibitors. Since DNA methylation is reversible, DNA methyltransferase inhibitors can be used to restore normal DNA methylation patterns, thereby reactivating genes involved in beneficial cellular functions such as controlling cellular proliferation, differentiation, apoptosis, and other homeostatic mechanism. Examples of such genes include cyclin dependent kinase 2a (p16), mutL homologue-1, and retinoblastoma. The scientific basis of this approach is discussed in detail by C. B. Yoo and P. A. Jones, *Nature Rev., Drug Discovery,* 2006, 5, 37-50, the entire disclosure of which is incorporated by reference.

There are four known DNA methyltransferase enzymes that have been characterized in detail, namely DNMT1, DNMT2, DNMT3a, and DNMT3b. In the DNA methyltransferases, the C-terminal catalytic domain is highly conserved. See B. Brueckner and F. Lyko, *Trends Pharmacol. Sci.,* 2004, 25, 551-54.

There are two classes of DNA methyltransferase inhibitors, nucleoside analogues and non-nucleosides. The nucleoside analogues have a modified cytosine ring attached to either a ribose or deoxyribose moiety. Inhibition by such analogues is believed to occur when the nucleoside analogue is incorporated into DNA. Other DNA methyltransferase inhibitors are non-nucloside analogues. Examples of DNA methyltransferase inhibitors that are nucleoside analogues include azacitidine (5-azacytidine), decitabine (5-aza-2'-deoxycytidine), 5-fluoro-2'-deoxycitidine, 5,6-dihydro-5-azacytidine (DHAC), zebularine (2'-O-t-butyldimethylsilyl-3'-O-[(diisopropylamino)(2-cyanoethoxy)phosphino]-5'-O-(4,4'-dimethoxytrityl)-2(1H)-pyrimidinone-1-β-D-riboside), fazarabine (1-β-D-arabinofuranosyl-5-azacytosine). Among these, azacitidine and decitabine are believed to be particularly useful since they have shown clinical efficacy in the treatment of haemotological malignancies such as acute myeloid leukemia. Examples of non-nucleoside DNA methyltransferase inhibitors include hydralizine, procaine, procainamide, epigallocatechin gallate, psammaplin A, and RG108 ((S)-2-(1,3-dioxo-1,3-dihydro-isoindol-2-yl)-3-(1H-indol-3-yl)-propionic acid).

Azacitidine

Azacitidine is 5-azacytidine, a nucleoside analogue with the structure:

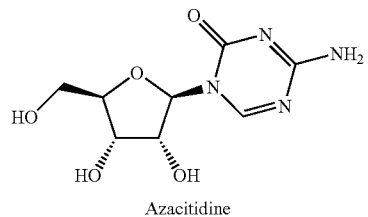 [SMILES: Nc1ncn([C@@H]2O[C@H](CO)[C@@H](O)[C@H]2O)c(=O)n1]

Azacitidine

The compound has been studied in a number of clinical trials for the treatment of both solid tumors and leukemia. For a detailed discussion, see J. Goffin and E. Eisnhauer, *Annals of Oncology,* 2002, 13, 1699, the complete disclosure of which is incorporated by reference. Azacitidine is approved by the United States Food and Drug Administration as a drug for the treatment of myelodysplastic syndrome. In a phase 3 clinical trial of azacitidine given as a subcutaneous dose of 75 mg/m$^2$/day for 7 days every 4 weeks to myelodysplastic syndrome patients, the response rate of 15% (5% of patients responded completely, and 10% of patients responded partially) was modest, albeit better than the complete lack of improvement seen in the control group. Details of the study are provided in the prescribing information for Vidaza™ (azacitidine) published by Pharmion Corporation, Aug. 31, 2004, the entire disclosure of which is incorporated by reference. Significant side-effects are seen with the drug, including nausea, anemia, thrombocytopenia, vomiting, pyrexia, leukopenia, diarrhea, fatigue, injection site erythema, constipation, neutropenia, and ecchymosis. In the clinical trials, leukopenia, thrombocytopenia and neutropenia were sufficiently serious to warrant reduction of the dose or discontinuation of treatment in some cases.

Because of a lack of available treatments for myelodysplastic syndrome and acute myeloid leukemia, and the toxicity and side effects associated with existing agents, the need exists for new therapies in the treatment of these diseases, particularly therapies that have greater potency and lower toxicity and/or activity across a broader spectrum of cell types. One solution would be a composition containing or method of using the above-mentioned therapeutic agents, wherein the efficacy is improved, for example by a synergistic combination with another compound. Such compositions or methods, could be very valuable in the treatment of myelodysplastic syndrome or acute myeloid leukemia. Using such compositions or methods in the treatment of myelodysplastic syndrome or acute myeloid leukemia could provide greater efficacy or potency, resulting in improved therapeutic response, diminished side effects, or both, as compared to using the above-mentioned chemotherapeutic agents alone.

SUMMARY OF THE INVENTION

Accordingly, we have invented a novel composition comprising a combination of antiproliferative agents, and a method for treating myelodysplastic syndrome and acute myeloid leukemia, comprising administering the antiproliferative agents in combination.

In one aspect of the invention, there is provided a composition comprising at least one compound according to Formula I:

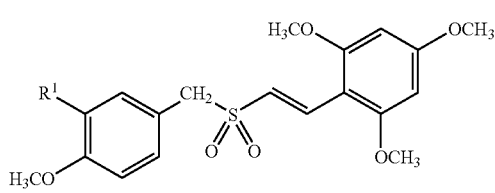

wherein R¹ is selected from the group consisting of —NH₂, —NH—CH₂—CO₂H, —NH—CH(CH₃)—CO₂H, and —NH—C(CH₃)₂—CO₂H, or a pharmaceutically acceptable salt of such a compound, and at least one DNA methyltransferase inhibitor, or a pharmaceutically acceptable salt thereof.

The preferred embodiments of the invention are those wherein the inhibitor inhibits human DNA methyltransferase enzymes, including one or more of the DNMT1, DNMT2, DNMT3a, and DNMT3b sub-types.

In one embodiment of the invention, the DNA methyltransferase inhibitor is a nucleoside analogue, or a pharmaceutically acceptable salt thereof.

In another embodiment of the invention, the DNA methyltransferase inhibitor is selected from the group consisting of azacitidine, decitabine, 5,6-dihydro-5-azacytidine, fazarabine, 5-fluoro-2'-deoxycitidine, zebularine, hydralizine, procaine, procainamide, epigallocatechin gallate, psammaplin A, or (S)-2-(1,3-dioxo-1,3-dihydro-isoindol-2-yl)-3-(1H-indol-3-yl)-propionic acid, or a pharmaceutically acceptable salt thereof, preferably azacitidine, decitabine, 5,6-dihydro-5-azacytidine, fazarabine, 5-fluoro-2'-deoxycitidine, or zebularine, or a pharmaceutically acceptable salt thereof, more preferably azacitidine or decitabine, or a pharmaceutically acceptable salt thereof, most preferably azacitidine, or a pharmaceutically acceptable salt thereof.

In preferred embodiments of the invention, the compound according to Formula I is (E)-2-(5-((2,4,6-trimethoxystyrylsulfonyl)methyl)-2-methoxyphenylamino)acetic acid, or a pharmaceutically acceptable salt thereof, preferably (E)-2-(5-((2,4,6-trimethoxystyrylsulfonyl)methyl)-2-methoxyphenylamino)acetic acid sodium salt ("Compound A").

Compound A

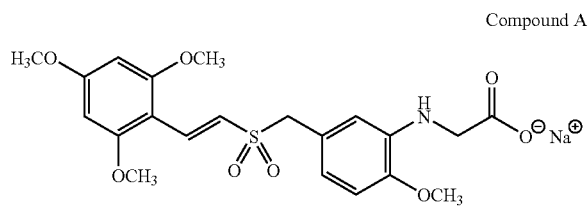 [SMILES: COc1cc(OC)c(/C=C/S(=O)(=O)Cc2ccc(OC)c(NCC(=O)[O-])c2)c(OC)c1 ; [Na+]]

In the most preferred embodiments of the invention, the compound according to Formula I is (E)-2-(5-((2,4,6-trimethoxystyrylsulfonyl)methyl)-2-methoxyphenyl-amino)acetic acid sodium salt and the DNA methyltransferase inhibitor is azacitidine.

In another aspect of the invention, there is provided the above-described composition of the invention, including any of the embodiments thereof, for use in medicine.

In another aspect of the invention, there is provided the use of the above-described composition of the invention, including any of the embodiments thereof, in the manufacture of a medicament for the treatment of myelodysplastic syndrome or acute myeloid leukemia.

In another aspect of the invention, there are provided methods of treating an individual for myelodysplastic syndrome or acute myeloid leukemia.

In one embodiment of this aspect of the invention, there are provided methods of treating an individual for myelodysplastic syndrome or acute myeloid leukemia comprising administering to the individual in need of such treatment, an effective amount of the composition of the invention. In particular and preferred embodiments of this aspect of the invention, the composition is any one of the above-described particular or preferred embodiments of the composition of the invention.

In another aspect of the invention, there is provided a method of treating an individual for myelodysplastic syndrome or acute myeloid leukemia, comprising administering to the individual in need of such treatment an effective amount of at least one compound according to Formula I as defined above, or a pharmaceutically acceptable salt of such a compound, and at least one DNA methyltransferase inhibitor, or a pharmaceutically acceptable salt thereof.

The preferred embodiments of this aspect of the invention are those wherein the inhibitor inhibits human DNA methyltransferase enzymes, including one or more of the DNMT1, DNMT2, DNMT3a, and DNMT3b sub-types.

In particular embodiments of this aspect of the invention, the DNA methyltransferase inhibitor is selected from the group consisting of azacitidine, decitabine, 5,6-dihydro-5-azacytidine, fazarabine, 5-fluoro-2'-deoxycitidine, zebularine, hydralizine, procaine, procainamide, epigallocatechin gallate, psammaplin A, or (S)-2-(1,3-dioxo-1,3-dihydro-isoindol-2-yl)-3-(1H-indol-3-yl)-propionic acid, or a pharmaceutically acceptable salt thereof, preferably azacitidine, decitabine, 5,6-dihydro-5-azacytidine, fazarabine, 5-fluoro-2'-deoxycitidine, or zebularine, or a pharmaceutically acceptable salt thereof, more preferably azacitidine or decitabine, or a pharmaceutically acceptable salt thereof, most preferably azacitidine, or a pharmaceutically acceptable salt thereof.

In particular embodiments of this aspect of the invention, the compound of Formula I is (E)-2-(5-((2,4,6-trimethoxystyrylsulfonyl)methyl)-2-methoxyphenylamino)acetic acid, or a pharmaceutically acceptable salt thereof, preferably (E)-2-(5-((2,4,6-trimethoxystyryl-sulfonyl)methyl)-2-methoxyphenylamino)acetic acid sodium salt In the most preferred embodiments of this aspect of the invention the compound according to Formula I is (E)-2-(5-((2,4,6-trimethoxystyrylsulfonyl)methyl)-2-methoxy-phenylamino)acetic acid sodium salt and the DNA methyltransferase inhibitor is azacitidine.

In another aspect of the invention, there is provided a kit comprising, in a first compartment, a compound according to Formula I as defined above, or a pharmaceutically acceptable salt of such a compound, and, in a second compartment, a DNA methyltransferase inhibitor, or a pharmaceutically acceptable salt thereof.

The preferred embodiments of this aspect of the invention are those wherein the inhibitor inhibits human DNA methyltransferase enzymes, including one or more of the DNMT1, DNMT2, DNMT3a, and DNMT3b sub-types.

In particular embodiments of this aspect of the invention, the DNA methyltransferase inhibitor is selected from the group consisting of azacitidine, decitabine, 5,6-dihydro-5-azacytidine, fazarabine, 5-fluoro-2'-deoxycitidine, zebularine, hydralizine, procaine, procainamide, epigallocatechin gallate, psammaplin A, or (S)-2-(1,3-dioxo-1,3-dihydro-isoindol-2-yl)-3-(1H-indol-3-yl)-propionic acid, or a pharmaceutically acceptable salt thereof, preferably azacitidine, decitabine, 5,6-dihydro-5-azacytidine, fazarabine, 5-fluoro-2'-deoxycitidine, or zebularine, or a pharmaceutically acceptable salt thereof, more preferably azacitidine or decitabine, or a pharmaceutically acceptable salt thereof, most preferably azacitidine, or a pharmaceutically acceptable salt thereof.

In particular embodiments of this aspect of the invention, the compound of Formula I is (E)-2-(5-((2,4,6-trimethoxystyrylsulfonyl)methyl)-2-methoxyphenylamino)acetic acid, or a pharmaceutically acceptable salt thereof, preferably (E)-2-(5-((2,4,6-trimethoxystyryl-sulfonyl)methyl)-2-methoxyphenylamino)acetic acid sodium salt In the most preferred embodiments of this aspect of the invention, the compound according to Formula I is (E)-2-(5-((2,4,6-trimethoxystyrylsulfonyl)methyl)-2-methoxy-phenylamino)acetic acid sodium salt and the DNA methyltransferase inhibitor is azacitidine.

In another aspect of the invention, there is provided the use of at least one compound according to Formula I, as defined above, preferably (E)-2-(5-((2,4,6-trimethoxystytylsulfonyl)methyl)-2-methoxyphenylamino)acetic acid, or a pharmaceutically acceptable salt thereof, most preferably (E)-2-(5-((2,4,6-trimethoxystyrylsulfonyl)methyl)-2-methoxyphenylamino)acetic acid sodium salt, in the manufacture of a medicament for administration concomitantly or sequentially with at least one DNA methyltransferase inhibitor, preferably azacitidine, decitabine, 5-fluoro-2'-deoxycitidine, 5,6-dihydro-5-azacytidine, zebularine, fazarabine, hydralizine, procaine, procainamide, epigallocatechin gallate, psammaplin A, or (S)-2-(1,3-fioxo-1,3-dihydro-isoindol-2-yl)-3-(1H-indol-3-yl)-propionic acid, or a pharmaceutically acceptable salt thereof, preferably azacitidine, decitabine, fazarabine, 5-fluoro-2'-deoxycitidine, 5,6-dihydro-5-azacytidine, or zebularine, or a pharmaceutically acceptable salt thereof, more preferably azacitidine, or decitabine, or a pharmaceutically acceptable salt thereof, most preferably azacitidine or a pharmaceutically acceptable salt thereof, for the treatment of myelodysplastic syndrome or acute myeloid leukemia.

It is to be understood that other particular and preferred embodiments of the invention will combine the features of particular and preferred embodiments explicitly described above. Embodiments defined by such combinations are contemplated as particular embodiments of the invention.

It is to be understood that both the foregoing general description and the following detailed description are exemplary and explanatory and are intended to provide further explanation of the invention as claimed.

Definitions

As used in the specification and the appended claims, the singular forms "a," "an" and "the" include plural referents unless the context clearly dictates otherwise.

As used herein, the terms "treat" and "treatment" are used interchangeably and are meant to indicate a postponement of development of a disorder and/or a reduction in the severity of symptoms that will or are expected to develop. The terms further include ameliorating existing symptoms, preventing additional symptoms, and ameliorating or preventing the underlying metabolic causes of symptoms.

As used herein, "individual" (as in the subject of the treatment) includes human beings and non-human animals, including both mammals and non-mammals. Mammals include, for example, humans; non-human primates, e.g. apes and monkeys; cattle; horses; sheep; and goats. Non-mammals include, for example, fish and birds.

The expression "effective amount" in connection with the treatment of a patient suffering from myelodysplastic syndrome or acute myeloid leukemia, refers to the amount of a composition, or of each active agent, according to the invention that inhibits the growth of cells that are proliferating at an abnormally high rate, or induces apoptosis of such cells, reduces the proportion of abnormal cells, or that maintains the disease in a state of complete or partial remission, or slows the progression of the disease.

Some of the compounds according to Formula I or the DNA methyltransferase inhibitors may be characterized by isomerism resulting from the presence of a chiral center. The isomers resulting from the presence of a chiral center comprise a pair of non-superimposable isomers that are called "enantiomers." Single enantiomers of a pure compound are optically active, i.e., they are capable of rotating the plane of plane polarized light. Single enantiomers are designated according to the Cahn-Ingold-Prelog system. *Advanced Organic Chemistry*, Jerry March, John 4th Edition (Wiley 1992), p. 109. Once the priority ranking of the four groups is determined, the molecule is oriented so that the lowest ranking group is pointed away from the viewer. Then, if the descending rank order of the other groups proceeds clockwise, the molecule is designated (R) and if the descending rank of the other groups proceeds counterclockwise, the molecule is designated (S). In the example shown in Scheme 1 below, the Cahn-Ingold-Prelog ranking is A>B>C>D. The lowest ranking atom, D, is oriented away from the viewer.

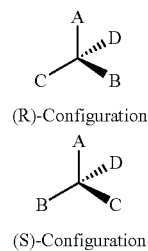

Scheme 1

Unless otherwise indicated, both absolute configurations and mixtures thereof are included in the scope of compounds of Formula I which contain a chiral center.

Reference to an optically active compound according to Formula I as an (R)- or (S)-enantiomer means that the compound contains the (R)- or (S)-enantiomer and is substantially free of the other enantiomer.

The expression "substantially free" of the other enantiomer means the (R)- and (S)-enantiomers of the compound of Formula I have been separated such that the composition contains 80% or more by weight of one of the two enantiomers. Preferably, the composition contains 90% or more by weight of a single enantiomer. More preferably, the composition contains 95% or more by weight of a single enantiomer. Most preferably, the composition contains 99% or more by weight of a single enantiomer.

Thus, by an (R)-enantiomer of a compound according to Formula I is meant a compound that is substantially free of the (S)-enantiomer and that the compound thereby comprises 80% or more by weight of its (R)-enantiomer and likewise contains 20% or less of its (S)-enantiomer as a contaminant by weight.

Isolated optical isomers may be purified from racemic mixtures by well-known chiral separation techniques. According to one such method, a racemic mixture of a compound having the structure of Formula I is separated into 99% pure optical isomers by HPLC using a suitable chiral column, such as a member of the series of the DAICEL® CHIRALPAK® family of columns (Daicel Chemical Industries, Ltd., Tokyo, Japan). The column is operated according to the manufacturer's instructions.

Nomenclature employed herein for providing systematic names for compounds disclosed herein may be derived using the computer program package CHEMDRAW®, CambridgeSoft Corporation, Cambridge, Mass. 02140.

DETAILED DESCRIPTION OF THE INVENTION

I. Treatment of Myelodysplastic Syndrome or Acute Myeloid Leukaemia

According to the present invention, compounds according to Formula I or a pharmaceutically acceptable salt thereof, and a DNA methyltransferase inhibitor, for example azacitidine, or a pharmaceutically acceptable salt thereof, are administered in combination to treat myelodysplastic syndromes or acute myeloid leukaemia.

A. Treatment of Myelodysplastic Syndrome

The compositions and methods according to the invention may be employed in therapy to individuals (animals, including mammals, including humans) suffering from myelodysplastic syndrome.

The compositions and methods of the invention are believed effective against myelodysplastic syndrome at any stage of the disease, and to retard progression of the disease, including progression to acute myeloid leukaemia. It is also believed that the compositions and methods of the invention will be effective to maintain the disease in complete or partial remission following treatment that has been effective in attaining such remission, for example bone marrow transplant or chemotherapy.

Thus, the compositions and methods of the invention are believed effective against any of the sub-classifications of the syndrome, as defined by either the FAB or WHO classifications, including refractory anemia with or without ringed sideroblasts, 5q-syndrome with or without ringed sideroblasts, refactory anemia with multilineage dysplasia with or without ringed sideroblasts, refactory anemia with excess blasts I and II, refractory anemia with excess blasts in transformation, chronic myelo-monocytic leukemia, and unclassifiable myelodysplastic syndrome.

It is also believed that the compositions and methods of the invention will be beneficial to treat patients within any of the classifications defined by the International Prognostic Scoring System, including the low, intermediate-1, intermediate-2 and high risk classifications. The compositions and methods of the invention are expected to be particularly beneficial in treating patients who are within the intermediate and high risk classifications and are at increased risk of death or progression of the disease to acute myeloid leukemia.

B. Treatment of Acute Myeloid Leukemia

The compositions and methods according to the invention may also be employed in therapy to individuals (animals, including mammals, including humans) suffering from acute myeloid leukemia.

The compositions and methods of the invention are believed effective against acute myeloid leukemia. It is also believed that the compositions and methods of the invention will be effective both to treat the active disease, as well as to maintain the disease in complete or partial remission following treatment that has been effective in attaining such remission, for example bone marrow transplant or chemotherapy.

The compositions and methods of the invention are believed effective against any of the sub-classifications of acute myeloid leukemia, as defined by either the FAB or WHO classifications, including minimally differentiated myeloid leukemia (MO), acute myeloid leukemia without maturation (M1), acute myeloid leukemia with maturation (M2), acute myeloid leukemia with maturation with t(8;21), acute promyelocytic leukemia (M3), hypergranular type acute myeloid leukemia, micro granular type acute myeloid leukemia. acute myelomonocytic leukemia (M4), acute myelomonocytic leukemia with increased marrow eosinophils (M4EO), acute Monocytic Leukemia (M5), acute monoblastic leukemia (M5a), acute monocytic leukemia with maturation (M5b), erythroleukemia, erythroid/myeloid leukemia (M6a), pure erythroid leukemia (M6b), acute megakaryoblastic leukemia (M7), acute megakaryoblastic leukemia associated with t(1;22), acute basophilic leukemia, acute myelofibrosis (acute myelodysplasia with myelofibrosis), acute leukemia and transient myeloproliferative disorder in Down's Syndrome, hypocellular acute myeloid leukemia, and myeloid sarcoma.

II. The Advantages of the Invention

We have discovered that when a compound of Formula I is combined with a DNA methyltransferase inhibitor a synergistic effect is seen with regard to cytotoxicity towards cells of the HL 60 human promyelocytic leukemia cell line. Specifically, the synergistic effect has been observed when (E)-2-(5-((2,4,6-trimethoxystyrylsulfonyl)methyl)-2-methoxyphenylamino)acetic acid sodium salt is combined with azacitidine in an experiment which is described in detail in Example 6 below. A method for analysis of the effect of a combination of drugs was described by T.-C. Chou and P. Talalay, *Trends Pharmacol. Sci.*, 1983, 4, 450-54. A combination index of 1.0 indicates a purely additive effect of the drugs, a combination index of greater than 1.0 indicates an antagonistic effect of the combination, while a combination index of less than 1.0 indicates a synergistic effect. Surprisingly, compared to the cytotoxic effects of the compounds individually, the combination (E)-2-(5-((2,4,6-trimethoxystyrylsulfonyl)methyl)-2-methoxyphenylamino)acetic acid sodium salt in various ratios with azacitidine showed a combination index of 0.3 to 0.75, indicating moderate to strong synergism.

The effect observed towards the HL-60 cell line is of particular relevance with regard to predicting therapeutic efficacy in myelodysplastic syndrome and acute myeloid leukemia because the HL-60 cell line was derived from a patient with acute promyelocytic leukemia. See S. J. Collins, *Blood*, 1987, 70(5), 1233-44. Azacitidine induces apoptosis in the HL-60 cell line. Subsequently, azacitidine has been shown to be effective clinically for the treatment of myelodysplastic syndrome, and is an FDA-approved treatment for myelodysplastic syndrome. It is believed that the surprising synergy observed with the combination of (E)-2-(5-((2,4,6-trimethoxystyrylsulfonyl)methyl)-2-methoxyphenyl-amino)acetic acid sodium salt and azacitidine predicts that the same combination will have enhanced potency or efficacy compared to either agent used alone in the clinical treatment of myelodysplastic syndrome.

In light of the surprising results observed in the above-described experiments, a beneficial synergistic effect is expected when a DNA methyltransferase inhibitor is used in combination with a compound of Formula I for the treatment of myelodysplastic syndrome of acute myeloid leukemia. Although the invention is not limited by theory, it is believed that because of the scientific consensus that the mechanism of action of azacitidine is through inhibition of DNA methyltransferase, the synergistic effect seen with azacitidine will be observed when other DNA methyltransferase inhibitors are substituted for azacitidine in the combination. In addition, it is noted that Formula I above defines a limited number of structurally very similar compounds, and it is believed that other compounds of Formula I will show similar effects, exerted through similar molecular mechanisms, as those observed for the representative compound of Formula I, (E)-2-(5-((2,4,6-trimethoxystyrylsulfonyl)-methyl)-2-methoxyphenylamino)acetic acid sodium salt. It is therefore expected that the surprising effect observed with (E)-2-(5-((2,4,6-trimethoxystyrylsulfonyl)methyl)-2-methoxyphenylamino)acetic acid sodium salt will also be observed when other compounds of Formula I are employed in combination with DNA methyltransferase inhibitors to treat myelodysplastic syndrome or acute myeloid leukemia. Finally, the strong scientific consensus as to the close relationship between myelodysplastic syndrome and acute myeloid leukemia indicates that the compounds are expected to be efficacious across the spectrum of the manifestations of both myelodysplastic syndrome and acute myeloid leukemia.

III. Preparation of Compounds According to Formula I (E)-α,β-unsaturated sulfones according to Formula I may be prepared, for example, by Knoevenagel condensation of 2,4,6-trimethoxybenzaldehyde [830-79-5] (Aldrich Chemical, catalog #13,871-1) with a suitably substituted 2-(benzylsulfonyl)acetic acid C (Scheme 2).

The procedure is described for synthesis of styryl sulfones by Reddy et al., *Acta. Chin:. Hung.*, 1984, 115, 269-71; Reddy et al., *Sulfur Lett.*, 1991, 13, 83-90; Reddy et al., *Synthesis*, 1984, (4), 322-23; and Reddy et al., *Sulfur Lett.*, 1987, 7, 43-48, and International Patent Application Publications WO03/072062 and WO05/089269, the entire disclosures of which are incorporated herein by reference. A general synthesis according to a Knoevenagel condensation is depicted in Scheme 2 below.

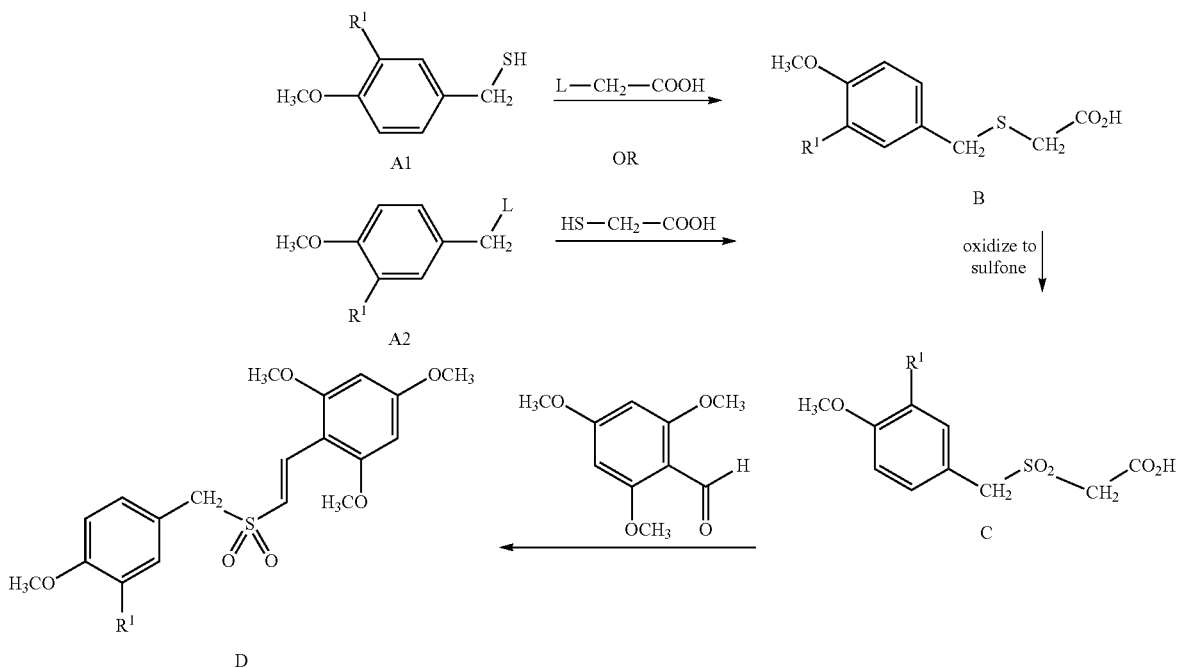

The intermediate benzylsulfonyl acetic acid C, employed in Scheme 2, may be prepared by oxidation of the corresponding benzylmercaptoacetic acids B. The benzyl mercaptoacetic acid B may be prepared by reacting mercaptoacetic acid [68-11-1] (Aldrich Chemical catalog #47,534-3) with compound A2 having a leaving group L, or by reacting an intermediate L-CH$_2$—CO$_2$H, e.g., a haloacetic acid with mercaptan A1.

In the reactions described herein for preparing compounds of Formula I, including the reactions depicted in Scheme 2, any R$^1$ groups present, and which may be reactive under the conditions of a particular reaction, may be protected during that reaction by protecting groups. Thus, preparation of compounds according to Formula I via the synthesis shown in Scheme 2 may in some instances include additional synthetic steps to add or remove a protecting group. Accordingly, for purposes of the synthesis in Scheme 2, the designation R$^1$ includes the functional groups previously listed: —NH$_2$, —NH—CH$_2$—CO$_2$H, —NH—CH(CH$_3$)—CO$_2$H, and —NH—C(CH$_3$)$_2$—CO$_2$H, and also includes those functional groups protected by protecting groups.

A "protecting group" is a chemical functionality which selectively blocks one or more reactive sites in a multifunctional compound such that a chemical reaction can be carried out selectively at another unprotected reactive site. Certain processes for preparation of compounds according to the present invention may rely upon protecting groups to block reactive functional groups that are present in the reactants. Examples of reactive groups which may be blocked by suitable protecting groups include —NH$_2$ groups which may be present. If such groups that are reactive under the conditions of a reaction step are not blocked by suitable protecting groups prior to reaction, unwanted side reactions may occur. For example, in a preparation according to Scheme 2, an —NH$_2$ group on the Formula A1 intermediate may react with the L-CH$_2$—CO$_2$H intermediate in addition to, and in competition with, the —SH group on the Formula A1 intermediate.

A protecting group may be introduced prior to carrying out a particular reaction that may affect a chemical group other than one that is desired. The protecting group is optionally removed at any suitable point in the synthesis after the reaction which necessitated use of the protecting group.

Protecting groups may be selected from any protecting groups described in the literature or known to the skilled chemist as suitable for the protection of the functional group which must be protected. Protecting groups may be introduced and removed by any suitable chemical synthesis method that is described in the art or known to the skilled chemist as suitable for the removal of the particular protecting group. Methods of removing protecting groups are preferably selected so as to effect selective removal of the protecting group with minimum effect on other chemical functionality in the molecule.

Protecting groups for R$^1$ that is —NH$_2$ include benzyl, 2,4-dimethoxybenzyl, CBZ, p-methoxybenzyloxycarbonyl, p-nitrobenzyloxycarbonyl, t-BOC, trifluoroacetyl. Methods for removal of hydroxy and amino protecting groups include, for example, acid, base, metal or enzyme-catalyzed hydrolysis for CBZ; acid or iodotrimethylsilane for removal of t-BOC groups; hydrogenation for benzyl and CBZ; and photolysis for o-nitrobenzyloxycarbonyl.

Protecting groups may also include different oxidation states of a chemical group. An example of such a protecting group is an aromatic nitro group in place of R$^1$, which may readily be reduced to an —NH$_2$ group.

Further examples of protecting groups can be found in *Protecting Groups in Organic Synthesis*, by Theodora W. Green and Peter G. M. Wuts, 3$^{rd}$ edition, published by Wiley & Sons, New York (1999) and *Compendium of Synthetic Organic Methods*, by Harrison et al., Vols. 1-8, published by Wiley & Sons 1971-1996, the entire disclosures of which are incorporated herein by reference.

IV. Administration of Therapy According to Methods of the Invention

Antiproliferative therapy administered according to the invention is achieved by administering a combination of at least one Formula I compound, or pharmaceutically acceptable salt of such a compound, and at least one DNA methyltransferase inhibitor, or a pharmaceutically acceptable salt thereof. The combination of at least Formula I compound or pharmaceutically acceptable salt of such a compound, and at least one DNA methyltransferase inhibitor or a pharmaceutically acceptable salt thereof, may further comprise, or be used in combination with, other drugs, for example other antiproliferative compounds, or drugs to control side-effects, for example anti-emetic agents.

In one embodiment of the invention, the combination of at least Formula I compound or pharmaceutically acceptable salt of such a compound, and at least one DNA methyltransferase inhibitor, or a pharmaceutically acceptable salt thereof, are co-formulated and used as part of a single pharmaceutical composition or dosage form. The compositions according to this embodiment of the invention comprise at least one Formula I compound or pharmaceutically acceptable salt of such a compound, and at least one DNA methyltransferase inhibitor, or a pharmaceutically acceptable salt thereof, in combination with a pharmaceutically acceptable carrier. In such compositions, the Formula I compound, or pharmaceutically acceptable salt thereof, and DNA methyltransferase inhibitor, or pharmaceutically acceptable salt thereof, may together comprise from 0.1 to 99.99 weight percent of the total composition. The compositions may be administered by any route and according to any schedule which is sufficient to bring about the desired therapeutic effect in the patient.

Alternatively, according to other embodiments of the invention, the combination of at least one Formula I compound or pharmaceutically acceptable salt of such a compound, and at least one DNA methyltransferase inhibitor, or a pharmaceutically acceptable salt thereof, may be formulated and administered as two or more separate compositions, at least one of which comprises at least one Formula I compound, or a pharmaceutically acceptable salt of such a compound, and at least one of which comprises at least one DNA methyltransferase inhibitor, or a pharmaceutically acceptable salt thereof. The separate compositions may be administered by the same or different routes, administered at the same time or different times, and administered according to the same schedule or on different schedules, provided the dosing regimen is sufficient to bring about the desired antiproliferative effect in the patient. When the drugs are administered in serial fashion, it may prove practical to intercalate administration of the two drugs, wherein a time interval, for example a 0.1 to 48 hour period, separates administration of the two drugs.

When the Formula I compound and DNA methyltransferase inhibitor are to be administered as separate drugs according to the methods of the invention, they may each be administered in the form of a pharmaceutical composition, comprising the active agent (i.e. either the Formula I compound or the DNA methyltransferase inhibitor agent) in combination with a pharmaceutically acceptable carrier. The active agent in such formulations may comprise from 0.1 to 99.99 weight percent.

Routes of administration include enteral, such as oral; and parenteral, such as intravenous, intra-arterial, intramuscular, intranasal, rectal, intraperitoneal, subcutaneous and topical routes. Preferably, compositions according to the invention are administered parenterally, more preferably intravenously or subcutaneously.

It will be appreciated that "administered" means the act of making a drug available to the patient such that a physiological effect is realized. Thus, contemplated within the scope of the present invention is the instillation of the Formula I compound or the DNA methyltransferase inhibitor or both in the body of the patient in a controlled or delayed release formulation, with systemic or local release of the active agents occurring at a later time and/or over a prolonged time interval. Thus, a depot of a first agent may be administered to the patient and the therapy component comprising the other agent may be administered prior to, subsequent to, or during the systemic release of the first agent.

By "pharmaceutically acceptable carrier" is meant any carrier, diluent or excipient which is compatible with the other ingredients of the formulation and not deleterious to the recipient. The active agents, whether as separate compositions or a combined composition, may be formulated into dosage forms according to standard practices in the field of pharmaceutical preparations. See Alphonso Gennaro, ed., *Remington's Pharmaceutical Sciences*, 18th Ed. (1990), Mack Publishing Co., Easton, Pa. Suitable dosage forms may comprise, for example, tablets, capsules, solutions, parenteral solutions, troches, suppositories, or suspensions.

For parenteral administration, the active agents may be mixed with a suitable carrier or diluent such as water, an oil (particularly a vegetable oil), ethanol, saline solution, aqueous dextrose (glucose) and related sugar solutions, glycerol, or a glycol such as propylene glycol or polyethylene glycol. Solutions for parenteral administration preferably contain a water-soluble salt of the active agents. Stabilizing agents, antioxidant agents and preservatives may also be added. Suitable antioxidant agents include sulfite, ascorbic acid, citric acid and its salts, and sodium EDTA. Suitable preservatives include benzalkonium chloride, methyl- or propyl-paraben, and chlorbutanol. The composition for parenteral administration may take the form of an aqueous or nonaqueous solution, dispersion, suspension or emulsion.

For oral administration, the active agents may be combined with one or more solid inactive ingredients for the preparation of tablets, capsules, pills, powders, granules or other suitable oral dosage forms. For example, the active agent may be combined with at least one excipient such as fillers, binders, humectants, disintegrating agents, solution retarders, absorption accelerators, wetting agents, absorbents or lubricating agents. According to one tablet embodiment, the active agent may be combined with carboxymethylcellulose calcium, magnesium stearate, mannitol and starch, and then formed into tablets by conventional tableting methods.

For the administration of DNA methyltransferase inhibitors the preferred route of administration is by intravenous or subcutaneous injection. The compound is preferably formulated in an aqueous solution or suspension. A solution may be injected intravenously, whereas a suspension is preferably injected subcutaneously. When the DNA methyltransferase inhibitor is azacitidine, the preferred formulation is a 1:1 by weight mixture of azacitidine and mannitol reconstituted by suspension in sterile water. The resulting suspension is then injected subcutaneously, preferably within an hour of reconstitution.

The specific doses of the two active agents employed in the composition and methods of the invention to obtain the therapeutic benefit will, of course, be determined by the particular circumstances of the individual patient. Such circumstances include the size, weight, age and sex of the patient, the nature and stage of the disease, the aggressiveness of the disease, and the route of administration.

For the DNA methyltransferase inhibitor, a starting point for the determination of a suitable dose is the dose at which the DNA methyltransferase inhibitor has been found to be safe and effective either alone or in combination with other chemotherapeutic agents. For marketed drugs, suitable doses and dosing protocols are recommended by the manufacturer and published, for example in the *Physician's Desk Reference*, 58th Edition (Thomson Healthcare, 2004), or 60th Edition (Thomson Healthcare, 2006), the entire disclosures of which are incorporated herein by reference. For both marketed drugs and investigational chemotherapeutic agents, suitable doses are recommended and published in the literature, in reports of clinical trials' of the compounds. The person skilled in the art will refer to such sources in determining a suitable dose and dosing protocol for any particular indication. Such established protocols are preferred, particularly when the DNA methyltransferase inhibitor is being administered in a separate composition from the compound of Formula I. Thus, in a preferred embodiment, the dosage, formulation, route and schedule of administration of azacitidine is carried out according to the known protocols for the drug.

The dose selected will depend on the particular compound being used and the route and frequency of administration. In general, suitable doses for human administration range from about 5 to about 400 mg/m$^2$, for example, about 50, 100, 200, or 300 mg/m$^2$, preferably about 10 to 100 mg/m$^2$, for example about 10, 20, 30, 50, 60, 85, or 100 mg/m$^2$. Typically, treatment may be given weekly, or every two, three, or four weeks, with individual treatments comprising an infusion of one or more doses, for example up to about seven daily bolus doses. For azacitidine, for example, the recommended dose is 75 mg/m$^2$, given daily by subcutaneous injection for seven days, the treatment cycle repeated every four weeks. The maximum recommended daily dose under such a regimen is 100 mg/m$^2$. Patients are also preferably pre-treated with an antiemetic agent to control vomiting.

When the DNA methyltransferase inhibitors are used in combination with compounds of Formula I in the compositions and methods of the invention, it is envisaged that the dose of the DNA methyltransferase inhibitors used may be comparable to those which have been found safe and effective with the compound alone or in other combinations with other agents. However, the ability to use lower doses of the DNA methyltransferase inhibitors in the combination is envisaged, and may be necessary due to the surprising greater cytotoxic efficacy observed in the combination as compared to when the DNA methyltransferase inhibitor is used alone; the DNA methyltransferase inhibitor may therefore be effective when used in the combination at a lower dose than that at which it is effective when used alone.

For the compound according to Formula I, the preferred daily dose is in the range of about 1 to about 10000 mg/m$^2$, more preferably from about 5 to about 5000 mg/m$^2$, still more preferably about 10 to about 3000 mg/m$^2$, most preferably about 50 to about 1000 mg/m$^2$, for example 100, 350, 500, or 750 mg/m$^2$. Because the compounds of Formula I are believed to be of much lower toxicity than the DNA methyltransferase inhibitors, in any embodiment of the intention, the preferred sub-embodiments of the invention are those wherein the dose of the compound of Formula I exceeds that of the DNA methyltransferase inhibitor. Preferred ratios of the dose of the DNA methyltransferase inhibitor to the dose of the compounds of Formula I are in the range from about 1:1 to about 1:2000, more preferably about 1:5 to about 1:500, most preferably about 1:20 to about 1:300, for example about 1:30, 1:65, 1:100, 1:125, or 1:250. The daily dose of the compound of Formula I may be given in a single dose, or may be divided, for example into two, three, or four doses, equal or unequal, but preferably equal, that comprise the daily dose. Such doses may be given as a bolus dose injected over, for example, about 1 to about 4 hours. Alternatively, the dose may be given by continuous intravenous infusion during the dosing period. The optimum dose and administration schedule for the compound of Formula I will depend on the dose and administration schedule of the chemotherapeutic agent. It is believed that for optimum advantage the compound of Formula I is administered at a frequency at least equal to that at which the DNA methyltransferase inhibitor is administered. However, it may also be advantageous to continue administering the compound of Formula I between doses of the DNA methyltransferase inhibitor, or to begin administration of the compound of Formula I before and/or continue administering the compound of Formula I after the administration of the doses of the DNA methyltransferase inhibitor, for example by starting administration of the compound of Formula I one or more days before and/or more days after each cycle of treatment with the DNA methyltransferase inhibitor.

V. Salts of Compounds Utilized in the Practice of the Invention

The active agents, namely, the compounds of Formula I, and DNA methyltransferase inhibitor, may, where the structure of the active agent permits, take the form of salts. The term "salts" embraces salts commonly used to form alkali metal salts and to form additional salts of free acids or free bases. The term "pharmaceutically-acceptable salt" refers to salts which possess toxicity profiles within a range so as to have utility in pharmaceutical applications.

Suitable pharmaceutically-acceptable acid addition salts may be prepared from an inorganic acid or from an organic acid. Examples of such inorganic acids are hydrochloric, hydrobromic, hydroiodic, nitric, carbonic, sulfuric, and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, stearic, alginic, β-hydroxybutyric, salicylic, galactaric and galacturonic acid.

Suitable pharmaceutically acceptable base addition salts of compounds useful in the compositions of the invention include, for example, metallic salts made from calcium, magnesium, potassium, sodium and zinc or organic salts made from N,N'-dibenzylethylenediamine, chloroprocaine, choline, diethanolamine, ethylenediamine, meglumine (N-methylglucamine) and procaine. For the compounds of Formula I containing a carboxyl group, alkali metal or alkaline earth metal salts are preferred. More preferred are alkali metal salts, particularly sodium salts. Preferred base addition salts of compounds according to Formula I include sodium salts of (E)-2-(5-((2,4,6-trimethoxystyrylsulfonyl)-methyl)-2-methoxyphenylamino)acetic acid, racemic-(E)-2-(5-((2,4,6-trimethoxystyryl-sulfonyl)methyl)-2-methoxyphenylamino) propanoic acid, (E)-(R)-2-(5-((2,4,6-trimethoxystyrylsulfonyl)methyl)-2-methoxyphenylamino)propanoic acid, (E)-(S)-2-(5-((2,4,6-trimethoxystyrylsulfonyl)methyl)-2-methoxyphenylamino)propanoic acid and (E)-2-(5-((2,4,6-trimethoxystyrylsulfonyl)methyl)-2-methoxyphenylamino)-2-methylpropanoic acid.

All of these salts may be prepared by conventional means from the corresponding compound according to Formula I or DNA methyltransferase inhibitor, and may be prepared by reacting, for example, the appropriate acid or base with the compound.

The practice of the invention is illustrated by the following non-limiting examples.

EXAMPLES

Example 1

Synthesis of (E)-2-(5-((2,4,6-trimethoxystyrylsulfonyl)methyl)-2-methoxy-phenylamino)acetic acid A. Methyl 2-(5-((2,4,6-trimethoxystyrylsulfonyl)methyl)-2-methoxyphenylamino)acetate To a stirred solution of methyl bromoacetate (5 mmol) and sodium acetate (5 mmol) in methanol (20 mL) was added (E)-5-((2,4,6-trimethoxystyrylsulfonyl)methyl)-2-methoxybenzenamine (1 mmol). The resulting mixture was heated to reflux temperature. The heated mixture was stirred at reflux temperature for 12 to 15 h. The heated mixture was then cooled and poured onto water ice (about 100 g). A precipitate formed. The precipitate was separated by filtration to provide the product in 85% yield. m.p. 182-185° C.

B. (E)-2-(5-((2,4,6-Trimethoxystyrylsulfonyl)methyl)-2-methoxyphenylamino)acetic acid Methyl 2-(5-((2,4,6-trimethoxystyrylsulfonyl)methyl)-2-methoxyphenylamino)acetate (1 g) was dissolved in a mixture of ethanol (8 mL) and 4% aqueous sodium hydroxide (50 mL). The solution was heated to reflux temperature and maintained at reflux temperature for 10 min thereby obtaining a clear solution. The mixture was then allowed to cool to ambient temperature (25° C.), and stirred for 3 h. After 3 h, concentrated hydrochloric acid was added dropwise until a precipitate formed. The precipitate was separated by filtration, washed with water and recrystallized from 2-propanol to provide the product (E)-2,4,6-trimethoxystyryl-3-(carboxymethylamino)-4-methoxybenzylsulfone in 80% yield. m.p. 128-131° C. NMR (DMSO-d6) δ 3.76 (s, 3H), 3.80 (s, 6H), 3.82 (s, 3H), 4.23 (s, 2H), 6.25 (s, 2H), 7.06-7.09 (d, 1H vinylic), 6.66-6.74 (m, aromatic).

Example 2

Synthesis of 5-((2,4,6-trimethoxystyrylsulfonyl)methyl)-2-methoxybenzenamine

A. 4-Methoxy-3-nitrobenzylbromide

A solution of 4-methyl-2-nitroanisole (25 mmol), N-bromosuccinimide (25 mmol) and benzoyl peroxide (2.5 mmol) in carbon tetrachloride (100 mL) was heated at reflux for 18 h. The heated mixture was then poured into water. A solid precipitate formed and was separated by filtration. The aqueous filtrate was extracted with carbon tetrachloride (3×50 mL). The extract was concentrated under reduced pressure to yield a solid product. The solid products (the filtered precipitate and product of evaporating the extract) were combined and recrystallized from ethyl acetate-hexane to yield 4-methoxy-3-nitro benzyl bromide as a crystalline product in 70-75% yield. m.p. 110-112° C.

B. 4-Methoxy-3-nitrobenzylthioacetic acid

To a cold solution of sodium hydroxide (9.75 g, 240 mmol) in methanol (200 mL) was added thioglycollic acid (11.25 g, 120 mmol) slowly over 30 min. Sodium thioglycollate precipitated and was redissolved by stirring and warming the mixture. The sodium thioglycollate solution was then cooled to room temperature and 4-methoxy-3-nitrobenzyl chloride (30.0 g, 120 mmol) was added in portions to reduce the intensity of exothermic reaction. The resulting mixture was heated to reflux temperature and maintained at reflux temperature for 4 h. The heated mixture was then cooled and poured onto crushed ice (1 kg) containing hydrochloric acid (50 mL). A precipitate formed. The precipitate was separated by filtration, washed with ice cold water and dried under vacuum to yield 30 g (95% yield) of the desired 4-methoxy-3-nitrobenzylthioacetic acid product. m.p. 130-132° C.

C. 4-Methoxy-3-nitrobenzylsulfonylacetic acid

4-Methoxybenzylthioacetic acid (10 g) was dissolved in glacial acetic acid (80 mL). Hydrogen peroxide (20 mL, 30%) was added in one portion and the resulting mixture was stirred at room temperature (25° C.) for 10 h. The mixture was then poured onto crushed ice (500 g). A yellow precipitate formed. The precipitate was separated by filtration, washed with cold water and dried to provide the crude 4-methoxy-3-nitrobenzylsulfonylacetic acid product in 55% yield. Recrystallization of the crude product from hot water yielded the purified product as a crystalline solid. m.p. 96-98° C.

D. 2-((E)-2-(4-Methoxy-3-nitrobenzylsulfonyl)vinyl)-1,3,5-trimethoxybenzene

To a solution of 4-methoxy-3-nitrobenzyl sulfonylacetic acid (4.5 g, 15.5 mmol) in 30 mL of glacial acetic acid was added 2,4,6-trimethoxybenzaldehyde (3.05 g, 15.5 mmol) and a catalytic amount of benzylamine (0.6 mL). The resulting mixture was heated at reflux temperature for 6 h. The reaction mixture was then concentrated under reduced pressure to yield a gummy material. The gum was triturated with 2-propanol to yield a solid product. The solid product was recrystallized from a mixture of acetic acid and 2-propanol to provide the 2((E)-2-(4-methoxy-3-nitrobenzylsulfonyl)vinyl)-1,3,5-trimethoxybenzene product in 28% yield. m.p. 186-187° C.

E. (E)-5-((2,4,6-Trimethoxystyrylsulfonyl)methyl)-2-methoxybenzenamine

The compound was prepared by reduction of 2-((E)-2-(4-methoxy-3-nitrobenzylsulfonyl)vinyl)-1,3,5-trimethoxybenzene. Two alternative methods of achieving the reduction are provided.

E1. (E)-5-((2,4,6-Trimethoxystyrylsulfonyl)methyl)-2-methoxybenzenamine (reduction Method 1)

A solution of 2-((E)-2-(4-methoxy-3-nitrobenzylsulfonyl) vinyl)-1,3,5-trimethoxybenzene (13 mmol) in acetone-water (10:5, 25 mL) was heated to 50° C. After 30 min, sodium hydrosulfite ($Na_2S_2O_4$, 26.3 mmol) was added slowly, and the mixture was heated at reflux (50° C.) for 1 h. The heated mixture was then cooled to room temperature (25° C.) and water (25 mL) was added. A solid precipitate formed and was separated by filtration. The filtered product was washed with aqueous sodium bicarbonate. The product was distributed between water and ethyl acetate. The ethyl acetate layer was separated and dried over anhydrous sodium sulfate. The ethyl acetate was removed under reduced pressure and the crude product obtained thereby was recrystallized from 2-propanol to yield the desired (E)-5-((2,4,6-trimethoxystyrylsulfonyl) methyl)-2-methoxybenzenamine product. m.p. 148-150° C.

E2. (E)-5-((2,4,6-Trimethoxystyrylsulfonyl)methyl)-2-methoxybenzenamine (reduction Method 2)

5% Pd/C wet (10% by weight of the nitro compound to be reduced) is charged into a flask. Pd/C is wetted with ethanol by slowly adding through the sides of the flask. 2-((E)-2-(4-Methoxy-3-nitrobenzylsulfonyl)vinyl)-1,3,5-trimethoxybenzene (10 mmol) is added to the flask and then ethanol is added sufficient to produce a 5 g/100 mL concentration of the starting nitro compound. The resulting mixture is heated to 50-60° C. Hydrazine hydrate (26 eq.) is added to the heated mixture over a period of 15-20 min. The resulting mixture is then heated at reflux temperature for 5-6 h. The progress of the reaction is monitored by thin layer chromatography (TLC). When the reaction is complete, the Pd/C is separated from the reaction mixture by filtration of the hot reaction mixture. The filtered solid is washed with hot ethanol. The volume of ethanol was reduced by 50% by distilling under reduced pressure. The reduced volume mixture is combined with an equal volume of ice cold water. The resulting mixture is stirred for 30 min. A solid precipitate forms. The precipitate is separated by filtration and dried under vacuum. The separated precipitate is recrystallized from 2-propanol to provide the (E)-5-((2,4,6-trimethoxystyrylsulfonyl)methyl)-2-methoxybenzenamine product.

Example 3

Synthesis of (E)-2-(5-((2,4,6-trimethoxystyrylsulfonyl)methyl)-2-methoxyphenylamino)propanoic acid

A. Methyl (E)-2-(5-((2,4,6-trimethoxystyrylsulfonyl) methyl)-2-methoxyphenylamino)-propanoate Sodium acetate (0.4 mol) was dissolved in methanol (200 mL). Methyl-2-bromopropionate (40 mmol) was added and the resulting mixture was heated at reflux for 10 min. The heated mixture was cooled to room temperature (25° C.), and (E)-5-((2,4,6-trimethoxystyrylsulfonyl)methyl)-2-methoxybenzenamine (0.1 mol) was added. The resulting mixture was heated at reflux for 1 h. The hot reaction mixture was allowed to cool to room temperature (25° C.), and then poured into ice water (500 mL). A solid precipitate formed. The precipitate was separated by filtration and recrystallized from ethanol to provide the desired methyl (E)-2-(5-((2,4,6-trimethoxystyrylsulfonyl)methyl)-2-methoxy-phenylamino)propanoate.

B. (E)-2-(5-((2,4,6-Trimethoxystyrylsulfonyl)methyl)-2-methoxyphenylamino)propanoic acid To a solution of methyl (E)-2-(5-((2,4,6-trimethoxystyrylsulfonyl)methyl)-2-methoxyphenylamino)propanoate (0.1 mol) in ethanol (200 mL), was added sodium hydroxide (20% aqueous solution, 200 mL). The resulting mixture was heated at reflux for 2.5 h. The reaction was monitored by TLC. When the reaction was complete, the volatiles were removed under vacuum and the resulting residue was acidified to pH 4 by addition of acetic acid. A solid precipitate formed. The precipitate was separated by filtration. The filtered solid was recrystallized twice from acetone to provide the desired (E)-2-(5-((2,4,6-trimethoxystyrylsulfonyl)methyl)-2-methoxyphenylamino)propanoic acid. m.p. 176-180° C.

Example 4

(E)-2-(5-((2,4,6-Trimethoxystyrylsulfonyl)methyl)-2-methoxyphenylamino)acetic acid sodium salt (E)-2-(5-((2,4,6-Trimethoxystyrylsulfonyl)methyl)-2-methoxyphenylamino)acetic acid (15 g, 0.032 mol) is dissolved in ethanol (150 ml) and 1N NaOH (1.28 g in 33 ml of water, 0.032 mol) is added, adjusted pH to 7.5-8.0 and stirred at room temperature for 1 h. The reaction is cooled to 0° C., and the precipitated solid is collected by filtration, washed with cold ethanol, and finally with hexane and dried under vacuum to give (E)-2-(5-((2,4,6-trimethoxystyrylsulfonyl)methyl)-2-methoxyphenylamino)acetic acid sodium salt (13 g, 84%).

Example 5

Cytotoxic effect of (E)-2-(5-((2,4,6-trimethoxystyrylsulfonyl)methyl)-2-methoxyphenylamino)acetic acid sodium salt combined with azacitidine towards HL-60 cells Human promyelocytic leukemia cell line HL-60 were obtained from American Type Culture Collection. The cells were maintained in RPMI 1640 medium supplemented with 10% FBS, penicillin, (50 U/mL), streptomycin, (50 µg/mL). Cell cultures were maintained at 37° C. in 5% $CO_2$ humidified atmosphere. Cells were counted in a hemocytometer, using Trypan blue staining as an indicator of viability.

The test compound, or combination of compounds, was added in 50 µL volume into flat-bottom 96-well plates. Control cultures received the same amount of medium without the test compound. HL-60 cells ($1\times10^6$ cells/mL) were suspended in growth medium and dispensed in 50 µL aliquots into the well containing the compound. The plates were incubated at 37° C. (5% $CO_2$) for 72 h. Cytotoxicity was then determined using the WST-1 assay. In the WST-1 assay cell viability is determined by incubating the cells for a further period of 0.5 to 4 h in the presence of the tetrazolium salt 4-(3-(4-iodophenyl)-2-(4-nitrophenyl)-2H-5-tetrazolio]-1,3-benzene disulfonate. In the presence of viable cells, the compound is reduced by mitochondrial dehydrogenases to a fluorescent product. The absorbance was measured against a background control without cell, in a microtiter plate reader (Bio-Tek Instruments, Elx 800) at 450 nm with a reference wavelength of 630 nm.

The effect of the combination of (E)-2-(5-((2,4,6-trimethoxystyrylsulfonyl)methyl)-2-methoxyphenylamino) acetic acid sodium salt with azacitidine, cytarabine, daunorubicin, zidovudine and paclitaxel on survival of the HL-60 cells was measured after 72 h of continuous exposure. Dose-response curves were generated for each drug alone to determine the concentration that produced 50% cell death ($IC_{50}$). The mean $IC_{50}$ values, shape (m), and conformity (r) were calculated by the median-effect method on the basis of at least three independent experiments. Combinations of drugs were then generated at concentrations below and above the $IC_{50}$ values of each drug. Initially, the effect of a simultaneous exposure of the cells to (E)-2-(5-((2,4,6-trimethoxystyrylsulfonyl)methyl)-2-methoxyphenylamino)acetic acid sodium salt and other agents for 72 h was tested. In the next series of experiments cells were exposed to various concentrations of first agent for 24 h, and then second agent was added for 48 hours. The WST-1 assay was performed after 72 h.

Linear curve fitting (median-effect analysis) was performed using CalcuSyn™ software to determine whether the effect of combining (E)-2-(5-((2,4,6-trimethoxystyrylsulfonyl)methyl)-2-methoxyphenylamino)acetic acid sodium salt and the various anticancer drugs was antagonistic, additive or synergistic by reference to the combination index determined by the CalcuSyn™ software using the methods described by T.-C. Chou and P. Talalay, *Trends Pharmacol. Sci.*, 1983, 4, 450-454. A combination index of 1.0 indicates an additive effect of the drugs, a combination index of greater than 1.0 indicates an antagonistic effect of the drugs, while a combination index of less than 1.0 indicates a synergistic effect.

Results

In the experiments described, 500 nM of (E)-2-(5-((2,4,6-trimethoxystyrylsulfonyl)methyl)-2-methoxyphenylamino) acetic acid sodium salt was the highest concentration that could be meaningfully studied, since higher concentrations resulted in virtually complete cell death at 72 h. The effects of combination of (E)-2-(5-((2,4,6-trimethoxystyrylsulfonyl) methyl)-2-methoxyphenylamino)acetic acid sodium salt and cytarabine, daunorubicin, zidovudine and paclitaxel ranged from strong antagonism to nearly additive. Only the combination of (E)-2-(5-((2,4,6-trimethoxystyrylsulfonyl)methyl)-2-methoxyphenylamino)acetic acid sodium salt with azacitidine showed a synergistic effect. As shown in Table 5, the combination index (C.I.) varied from 0.3 to 0.75 showing moderate to strong synergism.

TABLE 5

Combination index (CI) values from median-effect analysis[†]

| Drug Combination | | | | |
|---|---|---|---|---|
| Compound A (nM) | Azacitidine (nM) | Ratio | C.I.[‡] | Comment |
| 125 | 2000 | 1:63 | 0.44 | synergism |
| 125 | 4000 | 1:31 | 0.30 | strong synergism |
| 250 | 2000 | 1:125 | 0.68 | synergism |
| 250 | 4000 | 1:63 | 0.57 | synergism |
| 500 | 2000 | 1:250 | 0.63 | synergism |
| 500 | 4000 | 1:125 | 0.75 | moderate synergism |

[†]HL-60 cells (1 × 10⁶/mL) were first exposed to (E)-2-(5-((2,4,6-trimethoxystyrylsulfonyl)methyl)-2-methoxyphenylamino)acetic acid sodium salt ("Compound A") (125, 250, or 500 nM). After 24 h, azacitidine (2000 or 4000 µM) was added. The cytotoxic effect of the drug combination was evaluated at 72 h.
[‡]C.I. < 1 indicates synergism.

All references discussed herein are incorporated by reference. One skilled in the art will readily appreciate that the present invention is well adapted to carry out the objects and obtain the ends and advantages mentioned, as well as those inherent therein. The present invention may be embodied in other specific forms without departing from the spirit or essential attributes thereof and, accordingly, reference should be made to the appended claims, rather than to the foregoing specification, as indicating the scope of the invention.

The invention claimed is:

1. A method of treating an individual for myelodysplastic syndrome or acute myeloid leukemia, comprising administering to the individual in need of such treatment, an effective amount of a composition comprising at least one compound according to Formula I:

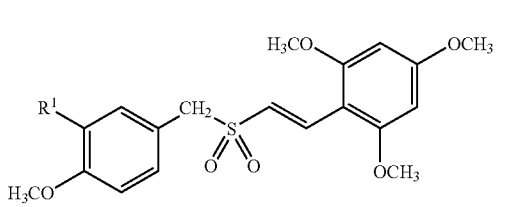

wherein $R^1$ is selected from the group consisting of —$NH_2$, —NH—$CH_2$—$CO_2H$, —NH—CH($CH_3$)—$CO_2H$, and —NH—C($CH_3$)$_2$—$CO_2H$, or a pharmaceutically acceptable salt of such a compound, and at least one DNA methyltransferase inhibitor selected from the group consisting of azacitidine, procaine, procainamide and epigallocatechin gallate, or a pharmaceutically acceptable salt thereof.

2. A method of treating an individual for myelodysplastic syndrome or acute myeloid leukemia, comprising administering to the individual in need of such treatment, an effective amount of at least one compound according to Formula I:

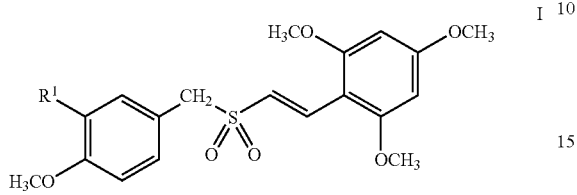

wherein R¹ is selected from the group consisting of —NH₂, —NH—CH₂—CO₂H, —NH—CH(CH₃)—CO₂H, and —NH—C(CH₃)₂—CO₂H, or a pharmaceutically acceptable salt of such a compound, and at least one DNA methyltransferase inhibitor selected from the group consisting of azacitidine, procaine, procainamide and epigallocatechin gallate, or a pharmaceutically acceptable salt thereof.

3. The method of claim 2, wherein the at least one DNA methyltransferase inhibitor is procaine or procainamide, or a pharmaceutically acceptable salt thereof.

4. The method of claim 2, wherein the at least one DNA methyltransferase inhibitor is epigallocatechin gallate, or a pharmaceutically acceptable salt thereof.

5. The method of claim 2, wherein the at least one DNA methyltransferase inhibitor is azacitidine, or a pharmaceutically acceptable salt thereof.

6. The method of claim 2, wherein the compound according to Formula I is (E)-2-(5-((2,4,6-trimethoxystyrylsulfonyl)methyl)-2-methoxyphenylamino)acetic acid, or a pharmaceutically acceptable salt thereof.

7. The method of claim 6, wherein the compound according to Formula I is (E)-2-(5-((2,4,6-trimethoxystyrylsulfonyl)methyl)-2-methoxyphenylamino)acetic acid sodium salt.

8. The method of claim 7, wherein the compound according to Formula I is (E)-2-(5-((2,4,6-trimethoxystyrylsulfonyl)methyl)-2-methoxyphenylamino)acetic acid sodium salt and the DNA methyltransferase inhibitor is azacitidine.

9. The method of claim 1, wherein the at least one DNA methyltransferase inhibitor is azacitidine, or a pharmaceutically acceptable salt thereof.

10. The method of claim 1, wherein the compound according to Formula I is (E)-2-(5-((2,4,6-trimethoxystyrylsulfonyl)methyl)-2-methoxyphenylamino)acetic acid, or a pharmaceutically acceptable salt thereof.

11. The method of claim 10, wherein the compound according to Formula I is (E)-2-(5-((2,4,6-trimethoxystyrylsulfonyl)methyl)-2-methoxyphenylamino)acetic acid sodium salt.

12. The method of claim 11, wherein the compound according to Formula I is (E)-2-(5-((2,4,6-trimethoxystyrylsulfonyl)methyl)-2-methoxyphenylamino)acetic acid sodium salt and the DNA methyltransferase inhibitor is azacitidine.

13. The method of claim 2, for treating an individual for acute myeloid leukemia.

14. The method of claim 2 for treating an individual for myelodysplastic syndrome.

15. The method of claim 1, for treating an individual for acute myeloid leukemia.

16. The method of claim 1, for treating an individual for myelodysplastic syndrome.

17. A kit comprising, in a first compartment, a compound according to Formula I:

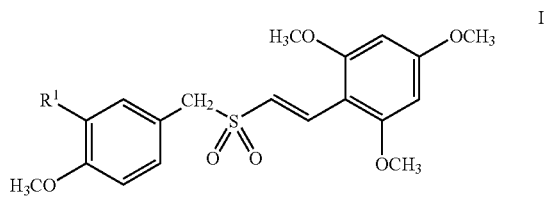

wherein R¹ is selected from the group consisting of —NH₂, —NH—CH₂—CO₂H, —NH—CH(CH₃)—CO₂H, and —NH—C(CH₃)₂—CO₂H, or a pharmaceutically acceptable salt of such a compound, and, in a second compartment, a DNA methyltransferase inhibitor selected from the group consisting of azacitidine, procaine, procainamide and epigallocatechin gallate, or a pharmaceutically acceptable salt thereof.

18. The kit of claim 17, wherein the at least one DNA methyltransferase inhibitor is azacitidine, or a pharmaceutically acceptable salt thereof.

19. The kit of claim 17, wherein the at least one DNA methyltransferase inhibitor is procaine or procainamide, or a pharmaceutically acceptable salt thereof.

20. The kit of claim 17, wherein the at least one DNA methyltransferase inhibitor is epigallocatechin gallate, or a pharmaceutically acceptable salt thereof.

21. The kit of claim 17, wherein the compound according to Formula I is (E)-2-(5-((2,4,6-trimethoxy styryl sulfonyl)methyl)-2-methoxyphenylamino)acetic acid, or a pharmaceutically acceptable salt thereof.

22. The kit of claim 17, wherein the compound according to Formula I is (E)-2-(5-((2,4,6-trimethoxystyrylsulfonyl)methyl)-2-methoxyphenylamino)acetic acid sodium salt.

23. The kit of claim 17, wherein the compound according to Formula I is (E)-2-(5-((2,4,6-trimethoxystyrylsulfonyl)methyl)-2-methoxyphenylamino)acetic acid sodium salt and the DNA methyltransferase inhibitor is azacitidine.

24. A composition comprising at least one compound according to Formula I:

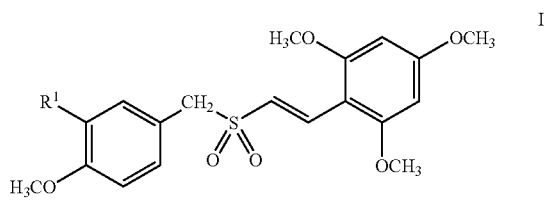

wherein R¹ is selected from the group consisting of —NH₂, —NH—CH₂—CO₂H, —NH—CH(CH₃)—CO₂H, and —NH—C(CH₃)₂—CO₂H, or a pharmaceutically acceptable salt of such a compound, and at least one DNA methyltransferase inhibitor selected from the group consisting of azacitidine, procaine, procainamide and epigallocatechin gallate, or a pharmaceutically acceptable salt thereof.

25. The composition of claim 24, wherein the at least one DNA methyltransferase inhibitor is azacitidine, or a pharmaceutically acceptable salt thereof.

26. The composition of claim 24, wherein the at least one DNA methyltransferase inhibitor is procaine or procainamide, or a pharmaceutically acceptable salt thereof.

27. The composition of claim 24, wherein the at least one DNA methyltransferase inhibitor is epigallocatechin gallate, or a pharmaceutically acceptable salt thereof.

28. The composition of claim 24, wherein the compound according to Formula I is (E)-2-(5-((2,4,6-trimethoxystyrylsulfonyl)methyl)-2-methoxyphenylamino)acetic acid, or a pharmaceutically acceptable salt thereof.

29. The composition of claim 24, wherein the compound according to Formula I is (E)-2-(5-((2,4,6-trimethoxystyrylsulfonyl)methyl)-2-methoxyphenylamino)acetic acid sodium salt.

30. The composition of claim 24, wherein the compound according to Formula I is (E)-2-(5-((2,4,6-trimethoxystyrylsulfonyl)methyl)-2-methoxyphenylamino)acetic acid sodium salt and the DNA methyltransferase inhibitor is azacitidine.

* * * * *